United States Patent [19]

Shaber et al.

[11] Patent Number: 5,240,925
[45] Date of Patent: Aug. 31, 1993

[54] FUNGICIDAL 2-ARYL-2-CYANO-2-(HETEROCYCLYLALKYL)ETHYL-1,2,4-TRIAZOLES

[75] Inventors: Steven H. Shaber, Horsham; Ted T. Fujimoto, Churchville, both of Pa.; Katherine E. Flynn, Fairfield, Ohio

[73] Assignee: Rohm and Haas Company, Philadelphia, Pa.

[21] Appl. No.: 749,840

[22] Filed: Aug. 26, 1991

[51] Int. Cl.$^5$ .................. A61K 31/41; C07D 249/08; C07D 401/06; C07D 405/06; C07D 409/06
[52] U.S. Cl. .................. 514/237.2; 514/336; 514/383; 544/132; 546/210; 546/276; 548/266.2; 548/266.6; 548/266.4; 548/267.4; 548/202; 548/236
[58] Field of Search .............. 548/266.4, 266.6, 267.4, 548/202, 236, 266.2; 514/383, 336, 235.8, 237.2; 544/132; 546/210, 276

[56] References Cited

U.S. PATENT DOCUMENTS

| | | | |
|---|---|---|---|
| 4,366,165 | 12/1982 | Miller et al. | 514/383 |
| 4,507,140 | 3/1985 | Sugavanam | 71/76 |
| 4,957,934 | 9/1990 | Boyle | 514/383 |
| 5,087,635 | 2/1992 | Shaber | 548/267.4 |

FOREIGN PATENT DOCUMENTS 319481 6/1989 European Pat. Off. .
2192184 1/1988 United Kingdom .

OTHER PUBLICATIONS

Mitsudera et al., J. Takeda Res. Lab., 41, 148–153 (1982).

*Primary Examiner*—Floyd D. Higel
*Attorney, Agent, or Firm*—Terry B. Morris

[57] ABSTRACT

This invention relates to 2-aryl-2-cyano-2-(heterocyclylalkyl)ethyl-1,2,4-triazoles of the formula

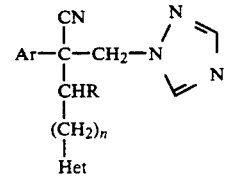

wherein Ar is an optionally substituted aryl group, Het is an optionally substituted five or six membered saturated or unsaturated heterocyclic ring containing one, two or three heteroatoms selected from oxygen, nitrogen and sulfur, or is a bicyclic unsaturated ring system containing up to ten atoms including one heteroatom selected from oxygen, nitrogen and sulfur, R is hydrogen or alkyl, n is zero or an integer of at least one, and the agronomically acceptable enantiomorphs, geometric isomers, acid addition salts and metal salt complexes thereof.

8 Claims, No Drawings

FUNGICIDAL 2-ARYL-2-CYANO-2-(HETEROCYCLYLALKYL-)ETHYL-1,2,4-TRIAZOLES

FIELD OF THE INVENTION

This invention relates to 2-aryl-2-cyano-2-(heterocyclylalkyl)ethyl-1,2,4-triazoles, their enantiomorphs, geometric isomers, acid addition salts and metal complexes, compositions containing these compounds, and the use of these compounds as fungicides.

BACKGROUND OF THE INVENTION

A number of aryl-alkyltriazoles are known to be useful as fungicides. For example, Miller, et al., U.S. Pat. No. 4,366,165 disclose 1- and 4-arylcyanoalkyl-1,2,4-triazoles as fungicidal agents. No heterocylic substituents are disclosed. Mitsudera et al., J. Takeda Res. Lab., Vol. 41, 148-153 (1982) teach the use of substituted $\alpha$-alkyl-$\alpha$-[(1,2,4-triazol-1-yl)methyl]-$\alpha$-arylacetonitriles as fungicides and plant growth regulators. No heterocyclylalkyl compounds are disclosed. Schneider, European Patent Application 0 319 481, discloses fungicidal 2-cyano-2-aryl-1-(azole-1-yl)ethane derivatives. The aryl is required to be phenyl which is substituted by an alkynyl group. Sugavanam, U.S. Pat. No. 4,507,140, discloses as fungicides a broad class of di- and tri-substituted butenyl, butynyl or butyl imidazoles and triazoles. However, none of this art suggest the specific class of triazoles of the present invention.

DESCRIPTION OF THE INVENTION

This invention relates to 2-aryl-2-cyano-2-(heterocyclylalkyl)ethyl-1,2,4-triazoles of the formula

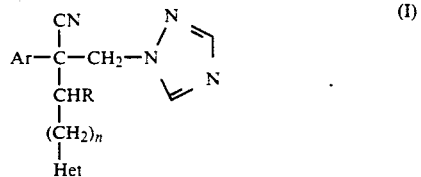

wherein

Ar is an optionally substituted aryl group,

Het is an optionally substituted five or six membered saturated or unsaturated heterocyclic ring containing one, two or three heteroatoms selected from oxygen, nitrogen and sulfur, or is a bicyclic unsaturated ring system containing up to ten atoms including one heteroatom selected from oxygen, nitrogen and sulfur, R is hydrogen or alkyl, n is zero or an integer of at least one, and the agronomically acceptable enantiomorphs, geometric isomers, acid addition salts and metal salt complexes thereof, compositions containing these compounds and their uses as fungicides, particularly against phytopathogenic fungi.

This invention relates to compounds of the general formula (I) wherein

Ar is a $(C_6-C_{10})$aryl group optionally substituted with one, two or three substituents, preferably with one or two substituents, each independently selected from the group consisting of halogen, $(C_1-C_4)$alkyl, halo$(C_1-C_4)$alkyl, $(C_1-C_4)$alkoxy, halo$(C_1-C_4)$alkoxy, $(C_1-C_4)$alkylthio, cyano, hydroxy, nitro, phenoxy, phenoxy mono-substituted with halogen, $(C_1-C_4)$alkyl, $(C_1-C_4)$alkoxy or trifluoromethyl, phenyl and phenyl mono-substituted with halogen, $(C_1-C_4)$alkyl, $(C_1-C_4)$alkoxy or trifluoromethyl;

Het is an optionally substituted five or six membered saturated or unsaturated heterocyclic ring containing one, two or three heteroatoms, preferably one or two heteroatoms, selected from oxygen, nitrogen and sulfur, or is a bicyclic unsaturated ring system containing up to ten atoms including one heteroatom selected from oxygen, nitrogen and sulfur;

R is hydrogen or $(C_1-C_4)$alkyl;

n is an integer from zero to about twenty; and the agronomically acceptable enantiomorphs, geometric isomers, acid addition salts and metal salt complexes thereof.

A preferred embodiment of this invention is the compounds, enantiomorphs, geometric isomers, salts and complexes of Formula (I) wherein Ar is naphthyl or, preferably, phenyl, each optionally substituted with one or two substituents independently selected from the group consisting of halogen, $(C_1-C_4)$alkyl, halo$(C_1-C_4)$alkyl, $(C_1-C_2)$alkoxy, halo$(C_1-C_2)$alkoxy, phenoxy, phenoxy mono-substituted with halogen, $(C_1-C_2)$alkyl, $(C_1-C_2)$alkoxy or trifluoromethyl, phenyl and phenyl mono-substituted with halogen, $(C_1-C_2)$alkyl, $(C_1-C_2)$alkoxy or trifluoromethyl;

Het is an optionally substituted furyl, benzofuryl, pyrrolyl, thienyl, benzothienyl, oxazolyl, isoxazolyl, pyrazolyl, imidazolyl, thiazolyl, isothiazolyl, oxadiazolyl, thiadiazolyl, triazolyl, pyridyl, quinolyl, isoquinolyl, pyrazinyl, pyrimidinyl, tetrahydrofuranyl, pyrrolidinyl, piperidinyl, tetrahydropyranyl, morpholinyl or piperazinyl and, when substituted, the Het moiety is substituted with one or two substituents each independently selected from the group consisting of $(C_1-C_2)$alkyl, halogen, acetyl and nitro;

R is hydrogen or methyl; and n is an integer from zero to about twelve.

A more preferred embodiment of this invention is the compounds, enantiomorphs, geometric isomers, salts and complexes of Formula (I) wherein Ar is phenyl or phenyl substituted with one or two substituents independently selected from the group consisting of halogen, $(C_1-C_2)$alkyl, halo$(C_1-C_2)$alkyl, $(C_1-C_2)$alkoxy and halo$(C_1-C_2)$alkoxy;

Het is selected from the group consisting of furyl, thienyl, 1,2,4-triazolyl, pyridyl, tetrahydrofuranyl, piperidinyl, tetrahydropyranyl, morpholinyl and piperazinyl, each optionally substituted with one or two substituents independently selected from halogen, $(C_1-C_2)$alkyl and acetyl; and R is hydrogen.

An even more preferred embodiment of this invention is the compounds, enantiomorphs, geometric isomers, salts and complexes of Formula (I) wherein Ar is selected from the group consisting of phenyl, phenyl substituted with one or two halogens selected from fluorine and chlorine and methoxyphenyl and Het is selected from the group consisting of tetrahydrofuran-2-yl, 4-morpholinyl, 2,6-dimethyl-4-morpholinyl, 2-pyridyl, 3-pyridyl, 2-thienyl, 1-piperidinyl, 1-methylpiperidin-3-yl, 2-furyl and tetrahydropyran-2-yl.

A most preferred embodiment of this invention is the compounds, enantiomorphs, salts and complexes of Formula (I) wherein Ar is phenyl, 4-chlorophenyl, 4-fluorophenyl, 2,4-dichlorophenyl or 2,4-difluorophenyl, Het is tetrahydrofuran-2-yl, 2-thienyl or 2-furyl and n is zero or one.

The term "Ar" (aryl) as used in the present specification means an aromatic ring structure of six to ten carbon atoms, preferably a phenyl or naphthyl group.

Typical aryl groups encompassed by this invention are phenyl, naphthyl, 4-chlorophenyl, 2,4-dichlorophenyl, 2,4,6-trichlorophenyl, 4-fluorophenyl, 2,4-difluorophenyl, 4-bromophenyl, 2,4-dibromophenyl, 4-iodophenyl, 2,4-dinitrophenyl, 4-methylphenyl, 2,4-dimethylphenyl, 4-ethylphenyl, 4-fluoro-2-methylphenyl, 2-chloro-4-methylphenyl, 4-t-butylphenyl, 4-(chloromethyl)phenyl, 2-(fluoromethyl)phenyl, 4-(2-chloroethyl)phenyl, 4-methoxyphenyl, 4-t-butoxyphenyl, 2-(trifluoromethyl)phenyl, 2-(difluoromethoxy)phenyl, 4-(trifluoromethoxy)phenyl, 4-(methylthio)phenyl, 4-(trichloromethyl)phenyl, 2-nitrophenyl, 4-nitrophenyl, 2,4-dicyanophenyl, 4-hydroxyphenyl, 3-isobutylphenyl, 2-methoxyphenyl, 2-(methylthio)phenyl, 4-cyanophenyl, 3-hydroxyphenyl, 4-(trifluoromethyl)phenyl, 4-phenylphenyl, 4-phenoxyphenyl, 4-(2'-methylphenoxy)phenyl, 4-(2'-methoxyphenoxy)phenyl, 4-(4'-(trifluoromethyl)phenoxy)phenyl, 4-(4'-chlorophenyl)phenyl, 2-(4'-methylphenyl)phenyl, 4-(2'-methoxyphenyl)phenyl, 4-(2'-(trifluorophenyl)phenyl and 2-chloro-4-(4'-chlorophenoxy)phenyl.

Typical Het groups encompassed by this invention are 2-furyl, 3-furyl, 5-methyl-2-furyl, 5-ethyl-2-furyl, benzo[b]fur-2-yl, pyrrol-1-yl, pyrrol-2-yl, 1-methylpyrrol-2-yl, 5-methylpyrrol-2-yl, 3,4-dimethylpyrrol-1-yl, 2-thienyl, 3-thienyl, 5-chloro-2-thienyl, 4-bromo-2-thienyl, 5-bromo-2-thienyl, 5-nitro-2-thienyl, 5-nitro-3-thienyl, 3-methyl-2-thienyl, 5-methyl-2-thienyl, benzo[b]thien-2-yl, oxazol-5-yl, 3,5-dimethylisoxazol-4-yl, 4-methylthiazol-5-yl, 2-methylisothiazol-4-yl, 4-methylisothiazol-2-yl, 4-methylisothiazol-5-yl, 1,3-imidazol-4-yl, 2-methyl-1,3-imidazol-5-yl, 1,3-imidazol-2-yl, 1,3-imidazol-5-yl, 1-methyl-1,3-imidazol-5-yl, 1,2,4-triazol-1-yl, pyrazol-1-yl, 3,5-dimethylpyrazol-1-yl, 2-pyridyl, 3-pyridyl, 4-pyridyl, 6-methyl-2-pyridyl, 3-methyl-2-pyridyl, 2-quinolyl, 4-quinolyl, 3-isoquinolyl, pyrazinyl, tetrahydrofuran-2-yl, 1-piperidinyl, 1-methylpiperidin-2-yl, 1-methylpiperidin-3-yl, 2,6-dimethylpiperidin-1-yl, 3-piperidinyl, tetrahydropyran-2-yl, 4-morpholinyl, 2,6-dimethyl-4-morpholinyl, 1-piperazinyl, 4-methylpiperazin-1-yl and 4-acetylpiperazin-1-yl.

Alkyl includes straight and branched alkyl groups, for example $(C_1-C_4)$alkyl such as methyl, ethyl, n-propyl, isopropyl, n-butyl, isobutyl, sec-butyl or t-butyl.

Alkoxy is, for example, $(C_1-C_4)$alkoxy such as methoxy, ethoxy and t-butoxy.

Alkylthio is, for example, $(C_1-C_4)$alkylthio such as methylthio, ethylthio and isopropylthio.

Halo means fluoro, chloro, bromo and iodo.

Haloalkyl is, for example, halo$(C_1-C_4)$alkyl such as chloromethyl, fluoromethyl, difluoromethyl, trifluoromethyl, 1-chloroethyl, 1,1-difluoroethyl, 3-chloropropyl, 1-bromo-2-methylpropyl and 2,3-dichloropropyl.

Haloalkoxy is, for example, halo$(C_1-C_4)$alkoxy such as difluoromethoxy, chloromethoxy, 2-bromoethoxy, 1,1-difluoroethoxy, 1,1-dibromopropoxy, and 1-chloro-2-methyl-2-propoxy.

This invention also includes the acid addition salts of the compounds of formula (I) wherein the anionic counterion of the acid is selected in such a manner that the sum of the valence charges of the protonated triazole compound and the anion equals zero.

This invention further includes the metal salt complexes of the compounds of formula (I) wherein the metal is a cation selected from Groups IIA, IVA, IB, IIB, VIB, VIIB and VIII of the Periodic Table and the anionic counterion of the metal is selected in such a manner that the sum of the valence charges of the cation and anion equals zero.

The 2-aryl-2-cyano-2-(heterocyclylalkyl)ethyl-1,2,4-triazoles of this invention can be prepared by conventional synthetic routes. For example, they may be prepared as shown by Scheme A:

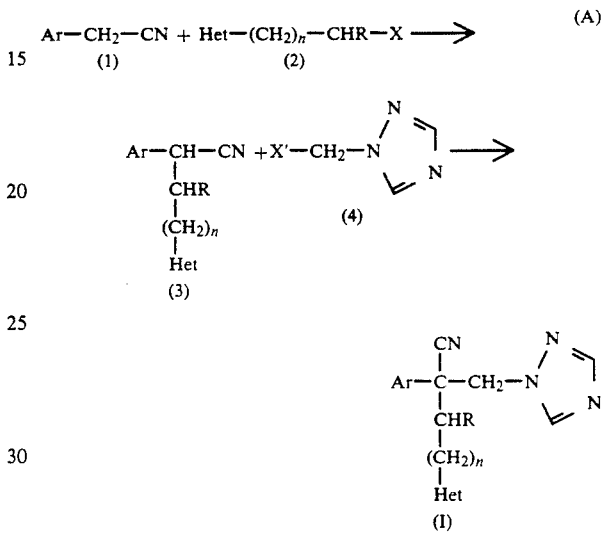

wherein Ar, Het, R and n are as described for Formula (I), X is a chloride, bromide, iodide, methylsulfonate, phenylsulfonate, 4-tolylsulfonate or any other leaving group capable of effecting the desired reaction, and X' is a chloride or bromide.

Processes for the alkylation of nitrile stabilized carbanions are disclosed in the literature, for example, S. Arseniyadis, K. S. Kyler and D. S. Watt in *Organic Reactions*, 31, pages 1–72 (general review) and pages 73–343 (specific examples), the disclosure of which is incorporated by reference herein.

Typical procedures employ an appropriately substituted arylmethyl cyanides (1) which is reacted with the heterocyclylalkyl chloride, bromide, iodide, methylsulfonate, phenylsulfonate or 4-tolylsulfonate (2) under basic conditions at a temperature from about −20° C. to about 100° C., preferably from about −10° C. to about 60° C. Examples of suitable bases include a Group IA metal, preferably sodium or potassium, hydroxide, hydride, t-butoxide, methoxide, and dimsylate. Hydride, t-butoxide and dimsylate bases are used in solvents such as toluene, dimethyl sulfoxide (DMSO), N,N-dimethylformamide (DMF), glyme, ether and tetrahydrofuran (THF). An alternative procedure to prepare the acetonitrile intermediate (3) employs phase transfer conditions in the presence of a base, such as a hydroxide, a solvent such as methylene chloride, chloroform, carbon tetrachloride, benzene, toluene, ethers, THF and dioxane. The phase transfer conditions usually require catalysts, examples of which include tetrabutylammonium hydroxide, tetrabutylammonium bromide, benzyltriethylammonium chloride or other quaternary ammonium salts, quaternary phosphonium salts and crown ethers, for example, 18-crown-6. The resulting 2-aryl-2-

(heterocyclylalkyl)acetonitrile (3) is preferably purified, for example, by distillation, and then reacted with about 1.1 equivalents of a base as described above at a temperature of from about 0° C. to about 50° C. with a 1-halomethyl-1,2,4-triazole (4), for example, 1-bromomethyl-1,2,4-triazole or, using about 2.2 equivalents of a base, with a salt, for example, the hydrochloride salt, of a 1-halomethyl-1,2,4-triazole (4), for example, 1-chloromethyl-1,2,4-triazole. The 1-halomethyl-1,2,4-triazole or a salt thereof may be added as a solid or a solution using as a solvent one of or a mixture of the solvents described in the procedure to form the acetonitrile intermediate (3). The product, a compound of Formula (I), may be recovered from the reaction mixture as a free base or as a salt by conventional methods, for example, adding an appropriate acid, such as hydrochloric acid, to precipitate the desired salt.

A variant of Scheme A may also be employed to prepare the compounds of this invention, except when Het is Het N-H as described in Scheme E, as shown by Scheme B:

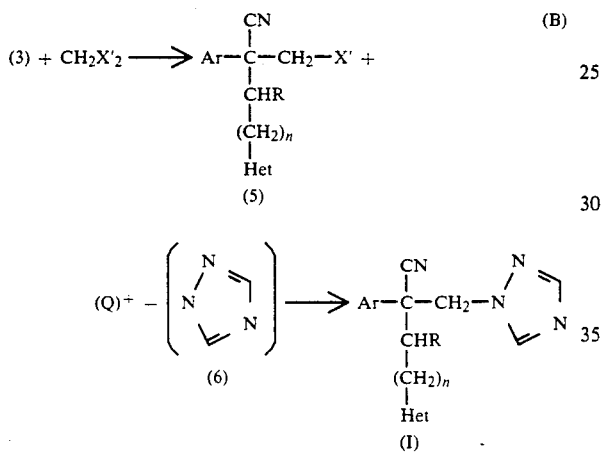

wherein Ar, Het, n, R and X' are as described previously in Scheme A and (Q)+ is the cation of an alkali metal, preferably sodium or potassium. The compound (5) is prepared by chloro- or bromomethylation of compound (3) with methylene chloride or methylene bromide, using from about one to about two equivalents of the methylene halide to the acetonitrile intermediate (3), under basic conditions at a temperature from about 0° C. to about 150° C., preferably from about 25° C. to about 60° C. Examples of suitable bases include a Group IA metal, preferably sodium or potassium, hydroxide, hydride, t-butoxide, and methoxide. Alternatively, phase transfer conditions can be used to prepare Intermediate (5) as described for Intermediate (3) in Scheme (A). The triazoles of this invention are then prepared by nucleophilic displacement of the chloro or bromo atom of compound (5) by a salt, preferably a Group IA metal salt such as potassium or sodium, of the triazole (6), using from about one to about three equivalents of the triazole salt for each equivalent of intermediate (5). This reaction can be run either neat or, preferably, in an appropriate solvent such as DMSO, DMF, toluene or xylene at a temperature of from about 0° C. to about 150° C., preferably from about 50° C. to about 130° C.

Processes for the preparation of alkyl halides from alcohols, nitriles from alkyl halides or other activated hydrocarbons, and reduction of esters or acids to alcohols are disclosed in the literature, for example, J. March, "Advanced Organic Chemistry: Reactions, Mechanism, and Structure," 3$^{rd}$ Edition, John Wiley and Sons (1985), the disclosure of which is incorporated by reference herein.

The substituted alkyl heterocycles (2) used in both Schemes A and B may be synthesized, if necessary, from commercially available materials using Scheme C:

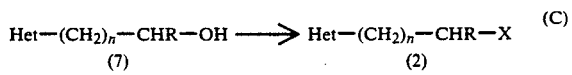

wherein Het, R, n, and X are as defined in Scheme A. The alcohol (7) may be reacted with a sulfonyl chloride, for example, methylsulfonyl chloride, in the presence of an acid acceptor, for example, triethylamine (TEA), either neat or in the presence of a suitable solvent, for example, THF, to form the heterocyclylalkyl methylsulfonate. Alternatively, the alcohol (7) may be reacted with a suitable halogenating agent, for example, thionyl chloride, triphenylphosphine plus carbon tetrachloride, and N-bromosuccinimide plus triphenylphosphine, either neat or in the presence of a suitable solvent, for example, chloroform.

The alkyl portion of the heterocyclylalkyl compound (2) can be readily homologated using known techniques, for example, as described in Scheme D:

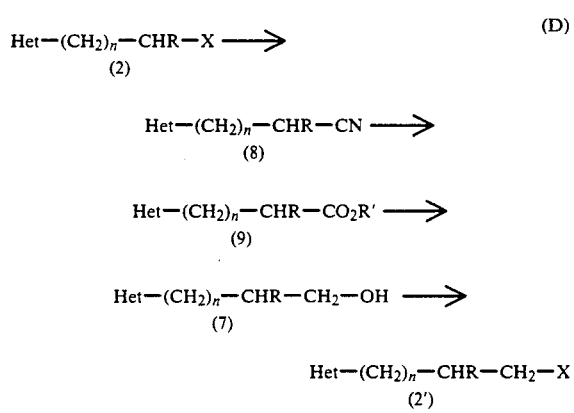

wherein Het, n and X are defined in Scheme A, R is hydrogen and R' is either hydrogen or alkyl, for example, methyl, ethyl, propyl and butyl. The heterocyclylalkyl chloride, bromide, iodide, methylsulfonate, phenylsulfonate or 4-tolylsulfonate (2) is reacted with a cyanide, for example, potassium or sodium, to provide the nitrile of formula (8). The nitrile is hydrolyzed with aqueous acid, for example, sulfuric acid, or aqueous base, for example, sodium hydroxide, to yield the carboxylic acid of formula (9) or the nitrile is reacted with a dry acid, for example, anhydrous hydrochloric acid, in the presence of an alcohol, for example, methyl or n-butyl alcohol, to yield a carboxylic ester of formula (9). The heterocyclylalkyl carboxylic acid or ester of formula (9) is reduced with, for example, lithium aluminum hydride or diborane, in a solvent such as dimethyl ether, THF, or dioxane to obtain its corresponding alcohol of formula (7). The alcohol of formula (7) is converted to a heterocyclylalkyl chloride, bromide, methylsulfonate, phenylsulfonate, or 4-tolylsulfonate (2') by methods identical to those described in Scheme C.

Heterocyclylalkyl chlorides, bromides, methylsulfonates, phenylsulfonates, and 4-tolylsulfonates of formula (2') containing a secondary nitrogen atom in the heterocyclyl moiety (Het N-H) formula (10), for example, 4-morpholinyl, the cis and trans isomers of 2,6-dimethyl-4-morpholinyl, piperidinyl, piperazinyl, and 1,2,4-triazolyl, can also be prepared using Scheme E:

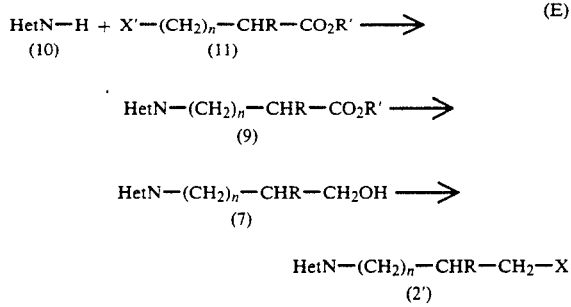

wherein X, n, and X' are defined in Scheme A, R is hydrogen and R' is an alkyl group, for example, methyl, ethyl, propyl or butyl. The secondary nitrogen containing heterocycle of formula (10) is alkylated by an alkyl haloester of formula (11), for example, ethyl 3-chloropropionate, methyl 2-chloropropionate, ethyl chloroacetate, ethyl 4-bromobutyrate, and methyl 11-bromoundecylate, in the presence of an acid acceptor, for example, triethylamine, either neat or in the presence of a suitable solvent, for example, toluene, THF, and carbon tetrachloride at a temperature from about −20° C. to about 120° C. to give the alkyl heterocyclylalkyl ester of formula (9). The ester of formula (9) is then reduced to the alcohol of formula (7) using procedures identical to those described in Scheme D. The alcohol of formula (7) is then converted to the heterocyclylalkyl compound of formula (2) using procedures identical to those described in Scheme C.

Alternatively, when Ar and Het are as described previously for Formula (I), R is hydrogen and n is zero, the resulting Formula (I) 2-aryl-2-cyano-2-(heterocyclylmethyl)ethyl-1,2,4-triazoles of this invention preferably can also be prepared from compounds of formula (12), for example, 2-furaldehyde, 2-thiophenecarboxaldehyde, and 3-pyridinecarboxaldehyde, using Scheme F:

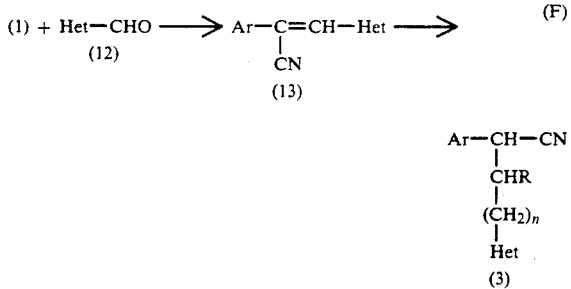

An unsaturated heterocyclylcarboxaldehyde of formula (12) whose carboxaldehyde group is attached to a carbon atom is reacted with a suitably substituted arylmethyl cyanide of formula (1) under basic conditions to obtain a substituted acrylonitrile intermediate (13) which is subsequently reduced with potassium, lithium or, preferably, sodium borohydride to produce a 2-aryl-2-(heterocyclylmethyl)acetonitrile of formula (3). This compound of formula (3) is then reacted as described in Scheme A to provide the 2-aryl-2-cyano-2-(heterocyclylmethyl)ethyl-1,2,4-triazole of formula (I) where n is zero and R is hydrogen.

The condensation of the arylmethyl cyanide (1) with the heterocyclylcarboxaldehyde (12) is conducted in a solvent, for example, an alcohol, ether, DMSO, DMF, toluene, a mixture thereof or water with one or more of these solvents, in the presence of a base at a temperature of from about −10° C. to about 80° C. Preferably, the reaction is performed in an alcohol, for example, methanol or ethanol, ether or toluene using a catalytic amount of an aqueous base, for example, sodium or potassium hydroxide, at a temperature of from about 0° C. to about 20° C. The intermediate acrylonitrile compound of formula (13) is reduced with potassium, or preferably, sodium borohydride in a solvent such as an alcohol, ether, THF, DMF or a mixture thereof at a temperature of from about 0° C. to about 50° C., preferably at about 5° C. to about 30° C., to produce the 2-aryl-2-(heterocyclylmethyl)acetonitrile of formula (3).

Furthermore, when Ar is as described previously for Formula (I), Het is an unsaturated heterocycle which is electron withdrawing, for example, pyridyl, R is hydrogen and n is one, the resulting Formula (I) 2-aryl-2-cyano-2-(heterocyclylethyl)ethyl-1,2,4-triazoles of this invention can be prepared from compounds of formula (14), for example, 2-vinylpyridine and 4-vinylpyridine, using Scheme G:

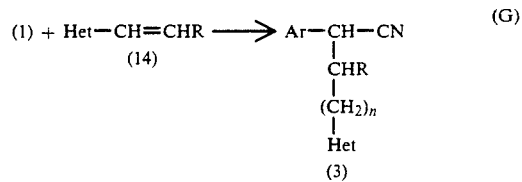

The unsaturated heterocyclylethylene of formula (14) is reacted with a suitably substituted arylmethyl cyanide of formula (1) under basic conditions to produce a 2-aryl-2-(heterocyclylethyl)acetonitrile of formula (3) where n is one and R is hydrogen. This compound of formula (3) is then reacted as described in Scheme A or B to provide the 2-aryl-2-cyano-2-(heterocyclylethyl)ethyl-1,2,4-triazole of formula (I) where n is one and R is hydrogen.

The alkylation of the arylmethyl cyanide (1) with the unsaturated heterocyclylethylene (14) is conducted in a polar solvent, for example, DMSO, DMF or a mixture thereof in the presence of a base at a temperature of from about 0° C. to about 120° C. Preferably, the reaction is performed in DMSO using a catalytic amount of a base, for example, sodium or potassium hydroxide and sodium or potassium amide, at a temperature of from about 25° C. to about 100° C. An alternative procedure is to employ phase transfer conditions in the presence of a base as described in Scheme A.

The acid addition salts of the 1,2,4-triazoles of this invention can be prepared by techniques which are well known in the art. A 1,2,4-triazole of Formula (I) can be dissolved in an appropriate polar solvent, for example, diethyl ether, THF, ethanol, methanol or combinations thereof, and reacted at a temperature from about 0° C. to about 50° C. with an equivalent or excess amount of a mineral or organic acid, for example, hydrochloric, sulfuric, nitric, phosphoric, and acetic which may or may not be dissolved in a solvent common to the solvent of the triazole solution. The mixture is then either cooled or evaporated to give an acid addition salt of the compounds of Formula (I) which can be either used as such or recrystallized from an appropriate solvent or combination of appropriate solvents, for example, methanol, chloroform, acetone, diethyl ether, and THF.

The metal salt complexes of the 1,2,4-triazoles of this invention can be prepared by adding dropwise, with stirring, a stoichiometric amount of a metal salt, for example, zinc (II) chloride and copper (II) chloride, dissolved in an appropriate solvent or combination of solvents to a solution of the 1,2,4-triazole. The reaction mixture is briefly stirred and the solvent is removed, for example, by distillation, to give a metal salt complex of the compounds of Formula (I).

An alternative preparation of these metal salt complexes involves mixing stoichiometric or excess amounts of the metal salt and a triazole of Formula (I) in a solvent containing adjuvants just prior to spraying the plants. Adjuvants that can be included in this in-situ formulation preparation are detergents, emulsifiers, wetting agents, spreading agents, dispersing agents, stickers, and adhesives which are used in agricultural applications.

Solvents that can be utilized in both of these procedures to prepare metal salt complexes include any polar solvent, for example, water, methanol, ethanol, isopropanol or ethylene glycol and any aprotic dipolar solvent, for example, DMSO, acetonitrile, DMF, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, and barium.

Examples of anions that can be used as the counterion in the metal salt include, but are not limited to, chloride, bromide, iodide, sulfate, bisulfate, phosphate, nitrate, perchlorate, carbonate, bicarbonate, hydrosulfide, hydroxide, acetate, oxalate, malate, and citrate.

Metal containing fungicides can also act as a safening agent when used in place of metal salts. Typical metal containing fungicides that can be utilized with the triazoles of this invention are: (1) dithiocarbamates and derivatives such as ferbam, ziram, maneb and its zinc ion coordination product mancozeb, and zineb; (2) copper based fungicides such as cuprous oxide, copper oxychloride, copper naphthenate and Bordeaux mixture; and (3) miscellaneous fungicides such as phenylmercuric acetate, N-ethylmercuri-1,2,3,6-tetrahydro-3,6-endomethano-3,4,5,6,7,7-hexachlorophthalimide, phenylmercuri monoethanolammonium lactate, nickel containing compounds and calcium cyanamide.

The compounds of this invention possess an asymmetric carbon atom and thus exist as racemic mixtures. The D and L enantiomorphs in these racemic mixtures can be separated via standard techniques such as fractional crystallization using, for example, D-tartaric acid, L-tartaric acid, and L-quinic acid followed by basification and extraction of the D or L enantiomorph free base.

When the heterocyclylalkyl group is saturated and multiply substituted at different carbon atoms of the ring, for example, the 2,6-dimethyl-4-morpholinylalkyl group, geometric (positional) isomerism occurs. The cis and trans isomers may, if desired, be separated from each other by techniques well known in the art, for example, fractional crystallization, fractional distillation, and selective extraction.

The following examples in Table 1 are provided to illustrate the present invention. Melting points are provided in the experimental section for those examples which are solids and NMR data are provided in Table 2 for examples whose physical state is a non-solid.

TABLE 1

$$\text{Ar}-\underset{\underset{\text{Het}}{|}}{\overset{\overset{\text{CN}}{|}}{\text{C}}}-\text{CH}_2-\text{N}\diagdown\underset{\diagup}{\overset{\diagdown}{\text{N}}}\diagdown\text{N}$$
$$(\text{CH}_2)_n$$

| Ex. No. | Ar | n | Het |
| --- | --- | --- | --- |
| 1 | phenyl | 1 | tetrahydrofuran-2-yl |
| 2 | 4-chlorophenyl | 2 | 4-morpholinyl |
| 3 | 4-chlorophenyl | 3 | 2,6-dimethyl-4-morpholinyl |
| 4 | 4-chlorophenyl | 2 | 2,6-dimethyl-4-morpholinyl |
| 5 | 4-chlorophenyl | 4 | 2,6-dimethyl-4-morpholinyl |
| 6 | 4-chlorophenyl | 11 | 2,6-dimethyl-4-morpholinyl |
| 7 | 4-chlorophenyl | 1 | 3-pyridyl |
| 8 | 4-chlorophenyl | 2 | 2-thienyl |
| 9 | 2-methoxyphenyl | 1 | 2-pyridyl |
| 10 | 2,4-dichlorophenyl | 3 | piperidin-1-yl |
| 11 | 2,4-dichlorophenyl | 1 | 1-methylpiperidin-3-yl |
| 12 | 4-chlorophenyl | 1 | 2-furyl |
| 13 | 4-chlorophenyl | 1 | 2-thienyl |
| 14 | 2-methoxyphenyl | 1 | tetrahydropyran-2-yl |
| 15 | phenyl | 2 | 2-pyridyl |

TABLE 2

| Ex. No. | Solvent | NMR Data 200 MHz, Delta Scale in ppm, Tetramethylsilane (TMS) Standard |
| --- | --- | --- |
| 1 | d$_6$-DMSO | 2.8(m, 6H), 3.5–3.6(m, 3H), 4.9(s, 2H), 7.4(m, 5H), 8.0(q, 2H) |
| 2 | CDCl$_3$ | 2.2–2.7(m, 8H), 3.6(t, 4H), 4.6(s, 2H), 7.3(s, 4H), 7.8(s, 1H), 8.0(s, 1H) |
| 3 | CDCl$_3$ | 1.1(d, 3H), 1.18(d, 3H), 1.45–2.8(m, 10H), 3.25–3.8(m, 2H), 4.65(brs, 2H), 7.38(s, 4H), 7.8(s, 2H) |
| 4 | CDCl$_3$ | 1.1(d, 3H), 1.18(d, 3H), 1.5–2.9(m, 8H), 3.2–3.8(m, 2H), 4.7(brs, 2H), 7.3(s, 4H), 7.8(s, 1H), 7.9(s, 1H) |
| 5 | CDCl$_3$ | 1.1(d, 3H), 1.23(d, 3H), 1.5–2.8(m, 12H), 3.3–3.7(m, 2H), 4.45(brs, 2H), 7.1–7.5(m, 4H), 7.8(s, 2H) |
| 6 | CDCl$_3$ | 1.1(d, 3H), 1.23(d, 3H), 1.3–2.2(m, 26H), 2.6–3.0(m, 2H), 4.6(brs, 2H), 7.3(s, 4H), 7.8(s, 1H), 7.9(s, 1H) |
| 7 | CDCl$_3$ | 3.4(s, 2H), 4.7(s, 2H), 7.0–7.7(m, 6H), 7.9–8.0(d, 2H), 8.2(s, 1H), 8.5(d, 1H) |
| 8 | CDCl$_3$ | 2.4–3.0(m, 4H), 4.6–4.8(q, 2H), 6.8–7.4(m, 3H), 7.4–7.7(q, 4H), 7.9(s, 2H) |
| 10 | CDCl$_3$ | 1.2–1.7(m, 8H), 2.0–2.4(m, 8H), 5.0(q, 2H), 7.2–7.5(m, |

TABLE 2-continued

| Ex. No. | Solvent | NMR Data 200 MHz, Delta Scale in ppm, Tetramethylsilane (TMS) Standard |
|---|---|---|
| 15 | CDCl₃ | 3H), 7.9(d, 2H) 2.5–2.9(m, 4H), 4.6–4.9(q, 2H), 7.0–7.5(m, 3H), 7.5(s, 5H), 7.8(s, 1H), 8.0(s, 1H), 8.5(d, 1H) |

EXAMPLE 1

Preparation of 1-[2-Cyano-2-phenyl-3-(tetrahydrofuran-2-yl)propyl]-1,2,4-triazole a. Preparation of Tetrahydrofurfuryl Bromide To a flask was added 40.9 grams (g.) (0.40 mole) of tetrahydrofurfuryl alcohol and 115.4 g. (0.44 mole) of triphenylphosphine. To the resultant white slurry was added 65.0 g. (0.37 mole) of N-bromosuccinimide over 2.5 hours while keeping the exothermic reaction below 30° C. After standing overnight, the thick pasty reaction mixture was heated on a steam bath and the resulting yellow liquid was removed by reduced pressure distillation using a Dean-Stark trap. The material was redistilled to obtain 55 g. of the tetrahydrofurfuryl bromide as a pale yellow liquid.

b. Preparation of 2-Phenyl-3-(tetrahydrofuran-2-yl)propionitrile

To a flask was added 6.0 g. (0.125 mole) of a 50% oil dispersion of sodium hydride. After washing the sodium hydride three times with 25 ml. portions of hexane to remove the oil, a solution of 11.7 g. (0.1 mole) of benzyl cyanide in 50 ml. of DMF was added over 2.5 hours. The reaction mixture became dark red. A solution of 18.4 g. (0.11 mole) of tetrahydrofurfuryl bromide in 25 ml. of DMF was added dropwise over 35 minutes and the flask contents stirred an additional 30 minutes. The mixture was poured into 1000 ml. of water and the organic material was extracted by four 250 ml. portions of ether. The combined ether extracts were then washed with two 250 ml. portions of water and once with 250 ml. of aqueous saturated sodium chloride solution (brine). After drying the washed extracts with sodium sulfate, they were treated with charcoal, filtered, and the ether distilled off to give 20 g. of dark green oil which was redistilled through a four inch Vigreux column yielding 9.1 g. of the desired 2-phenyl-3-(tetrahydrofuran-2-yl)propionitrile as a clear, colorless liquid boiling at 110°–111° C. at 0.15 mm of mercury (Hg).

c. Preparation of 1-Bromo-2-cyano-2-phenyl-3-(tetrahydrofuran-2-yl)propane

To a flask was added 9.1 g. (0.04 mole) of the 2-phenyl-3-(tetrahydrofuran-2-yl)propionitrile and 15.6 g. (0.09 mole) of methylene bromide followed by dropwise addition of 10.7 g. (0.13 mole) of a 50% aqueous sodium hydroxide solution over 15 minutes. The mixture was stirred and heated at 75° C. overnight, then at room temperature for two days and again heated overnight to obtain a 95% completed reaction. The flask contents were poured into 200 ml. of water and extracted three times with 100 ml. portions of ether. The combined ether extracts were washed two times with 100 ml. portions of water and once with 100 ml. of brine. The washed extracts were dried with sodium sulfate, filtered, and the ether stripped to yield 11 g. of the desired 1-bromo-2-cyano-2-phenyl-3-(tetrahydrofuran-2-yl)propane as a yellow oil.

d. Preparation of 1-[2-Cyano-2-phenyl-3-(tetrahydrofuran-2-yl)propyl]-1,2,4-triazole The 1-bromo-2-cyano-2-phenyl-3-(tetrahydrofuran-2-yl)propane, 8 g. (0.025 mole), was added to a solution of 8 g. (0.074 mole) of the potassium salt of 1H-1,2,4-triazole in 50 ml. of DMSO and heated at 75° C. overnight. Four angstrom size molecular sieves were added and the reaction was reheated to 75° C. for six days. The reaction was quenched with 1000 ml. of water and the organic material extracted four times with 250 ml. portions of ether. The combined ether extracts were washed two times with 200 ml. portions of water and once with 200 ml. of brine. The washed extracts were dried using sodium sulfate, filtered and the ether stripped to yield 3.2 g. of 1-[2-cyano-2-phenyl-3-(tetrahydrofuran-2-yl)-propyl]-1,2,4-triazole as an amber oil.

EXAMPLE 2

Preparation of 1-[2-(4-Chlorophenyl)-2-cyano-4-(4-morpholinyl)-butyl]-1,2,4-triazole a. Preparation of 2-(4-Chlorophenyl)-4-(4-morpholinyl)butyronitrile To a flask was added 1.4 g. (0.033 mole) of a 55% oil dispersion of sodium hydride. After washing the sodium hydride with hexane to remove the mineral oil, 20 ml. of a 2 to 1 mixture of toluene and DMF was added followed by the slow addition of 5.0 ml. (0.033 mole) of 4-chlorobenzyl cyanide. The resulting deep burgundy solution was stirred for one hour. The hydrochloride salt of 4-(2-chloroethyl)morpholine, 6.4 g. (0.033 mole), was neutralized with sodium hydroxide in a separate vessel and the resulting 4-(2-chloroethyl)morpholine free base was dissolved in 10 ml. of a 2 to 1 mixture of toluene and DMF. The free base solution was added slowly to the 4-chlorobenzyl cyanide solution at 0° C. and the reaction stirred at room temperature for two days. The reaction was poured into ice water and the organic layer extracted with ether. The ether extract was washed twice with 10% aqueous hydrochloric acid, the aqueous material made basic using concentrated ammonium hydroxide, and the desired free base material extracted into ethyl acetate. The ethyl acetate solution was dried, filtered, and concentrated. The crude product was purified by flash chromatography to give 3.7 g. (42% yield) of 2-(4-chlorophenyl)-4-(4-morpholinyl)butyronitrile as a yellow oil.

b. Preparation of 1-[2-(4-Chlorophenyl)-2-cyano-4-(4-morpholinyl)butyl]-1,2,4-triazole To a flask was added 0.24 g. (5.5 mmoles) of a 55% oil dispersion of sodium hydride. After washing the sodium hydride with hexane to remove the mineral oil, 25 ml. of DMF was added, the solution cooled to 0° C., and then 1.3 g. (5.0 mmoles) of 2-(4-chlorophenyl)-4-(4-morpholinyl)butyronitrile in 15 ml. of DMF was slowly added. The solution was stirred for 30 minutes and then 0.59 g. (5.0 mmoles) of 1-(chloromethyl)-1,2,4-triazole in 10 ml. of DMF was added slowly. The reaction was stirred overnight at room temperature and then was poured into ice water. The organics were extracted into ethyl acetate, washed with water, dried over magnesium sulfate, filtered, and concentrated. The product was purified using chromatography by eluting the impurities with ethyl acetate and the desired 1-[2-(4-chlorophenyl)-2-cyano-4-(4-morpholinyl)butyl]-1,2,4-triazole product with acetone to give 1.0 g. (58% yield) of an orange oil.

EXAMPLE 3

Preparation of
1-[2-(4-Chlorophenyl)-2-cyano-5-(2,6-dimethyl-4-morpholinyl)pentyl]-1,2,4-triazole a. Preparation of Ethyl 3-(2,6-dimethyl-4-morpholinyl)propionate This intermediate (26.0 g.) was prepared using the procedure described in Example 4a except using 24.5 ml. (0.2 mole) of 2,6-dimethylmorpholine, 19.2 ml. (0.20 mole) of ethyl 3-chloropropionate, and 30.3 ml. (0.22 mole) of triethylamine in 60 ml. of toluene and was isolated as a colorless liquid boiling 88°–88.5° C. at 5 mm of Hg.

b. Preparation of 4-(3-Hydroxypropyl)-2,6-dimethylmorpholine

This intermediate (14 g.) was prepared using the procedure described in Example 4b except using 17.82 g. (0.1 mole) of ethyl 3-(2,6-dimethyl-4-morpholinyl)propionate and 15.2 g. (0.4 mole) of lithium aluminum hydride in 200 ml. of dimethyl ether and then was isolated as a very pale yellow liquid.

c. Preparation of 4-(3-Chloropropyl)-2,6-dimethylmorpholine

This intermediate (2.3 g.) was prepared using the procedure described in Example 4c except using 5.0 g. (28 mmoles) of 4-(3-hydroxypropyl)-2,6-dimethylmorpholine and 9.5 g. (30 mmoles) of triphenylphosphine in 50 ml. of carbon tetrachloride and was isolated as a colorless liquid.

d. Preparation of 2-(4-Chlorophenyl)-5-(2,6-dimethyl-4-morpholinyl)valeronitrile This intermediate (2.0 g.) was prepared using the procedure described in Example 2a except using 2.3 g. (11 moles) of 4-(3-chloropropyl)-2,6-dimethylmorpholine, 0.48 g. of sodium hydride, and 1.69 g. (11 mmoles) of 4-chlorobenzyl cyanide in 15 ml. of a 2 to 1 mixture of toluene and DMF and was isolated as a pale yellow oil.

e. Preparation of 1-[2-(4-Chlorophenyl)-2-cyano-5-(2,6-dimethyl-4-morpholinyl)pentyl]-1,2,4-triazole This compound (1.2 g.) was prepared using the procedure described in Example 2b except using 1.0 g. (3.3 mmoles) of 2-(4-chlorophenyl)-5-(2,6-dimethyl-4-morpholinyl)valeronitrile, 0.38 g. (3.3 mmoles) of 1-(chloromethyl)-1,2,4-triazole, and 0.16 g. (3.6 mmoles) of sodium hydride in 35 ml. of DMF and was isolated as a yellow oil.

EXAMPLE 4

Preparation of
1-[2-(4-Chlorophenyl)-2-cyano-4-(2,6-dimethyl-4-morpholinyl)pentyl]-1,2,4-triazole a. Preparation of Ethyl 2,6-Dimethyl-4-morpholinylacetate To a flask was added 61.5 ml. (0.5 mole) of 2,6-dimethylmorpholine and 76.0 ml. (0.55 mole) of triethylamine in 150 ml. of toluene. The stirred solution was cooled to 0° C. and then 53.5 ml. (0.5 mole) of ethyl chloroacetate was added slowly. The reaction was heated to reflux and, after three hours, the mixture was cooled to room temperature, filtered, and the solvent removed. The residue was fractionally distilled to yield 70.3 g. (80%) yield of ethyl 2,6-dimethyl-4-morpholinylacetate boiling 81°–82° C. at 5 mm of Hg.

b. Preparation of 4-(2-Hydroxyethyl)-2,6-dimethylmorpholine

To a flask was added 22.8 g. (0.6 mole) of lithium aluminum hydride in 300 ml. of dimethyl ether. The stirred slurry was cooled to 0° C. and then 26.5 g. (0.15 mole) of ethyl 2,6-dimethyl-4-morpholinylacetate was slowly added. The reaction was allowed to warm to room temperature and stirred for 18 hours. It was then quenched with aqueous ammonium chloride, filtered, and extracted with diethyl ether. The solvent was concentrated to give 15.5 g. (67% yield) of the desired intermediate.

c. Preparation of 4-(2-Chloroethyl)-2,6-dimethylmorpholine

To a flask was added 5.0 g. (0.03 mole) of 4-(2-hydroxyethyl)-2,6-dimethylmorpholine in 50 ml. of carbon tetrachloride followed by 10.2 g. (0.04 mole) of triphenylphosphine. The mixture was stirred at reflux for three hours, then the reaction was cooled to 0° C., the triphenylphosphine oxide was filtered and the solvent stripped. The residue was dissolved in 10% aqueous hydrochloric acid and the by-products were extracted into ethyl acetate. The acid layer was then basified with ammonium hydroxide and extracted into ethyl acetate. The ethyl acetate solution was dried with magnesium sulfate, filtered, and concentrated. The crude product was further purified by flash chromatography to give 2.31 g. (43% yield) of 4-(2-chloroethyl)-2,6-dimethylmorpholine as a colorless liquid.

d. Preparation of 2-(4-Chlorophenyl)-4-[4-(2,6-dimethylmorpholinyl)]butyronitrile This intermediate (2.28 g.) was prepared using the procedure described in Example 2a except using 0.56 g (0.013 mole) of sodium hydride, 1.96 g. (0.013 mole) of 4-chlorobenzyl cyanide in 10 ml. of a 2 to 1 mixture of toluene and DMF, and 2.3 g. (0.013 mole) of 4-(2-chloroethyl)-2,6-dimethylmorpholine in 5 ml. of a 2 to 1 mixture of toluene and DMF.

e. Preparation of 1-[2-(4-Chlorophenyl)-2-cyano-4-(2,6-dimethyl-4-morpholinyl)butyl]-1,2,4-triazole One gram of this compound was obtained as a yellow oil using the procedure of Example 2b except using 1.0 g. (3.42 mmoles) of 2-(4-chlorophenyl)-4-[4-(2,6-dimethylmorpholinyl)]butyronitrile, 0.16 g. (3.76 mmoles) of sodium hydride, and 0.40 g. (3.42 mmoles) of 1-(chloromethyl)-1,2,4-triazole in 10 ml. of a 2 to 1 mixture of toluene and DMF.

EXAMPLE 5

Preparation of
1-[2-(4-Chlorophenyl)-2-cyano-6-(2,6-dimethyl-4-morpholinyl)hexyl]-1,2,4-triazole a. Preparation of Ethyl 4-(2,6-Dimethyl-4-morpholinyl)butyrate This intermediate (37.8 g.) was prepared using the procedure described in Example 4a except using 24.5 ml. (0.2 mole) of 2,6-dimethylmorpholine, 28.6 ml. (0.2 mole) of ethyl 4-bromobutyrate, 30.3 ml. (0.2 mole) of triethylamine, and 60 ml. of toluene and was isolated as a colorless liquid boiling 96.5°–97° C. at 4 mm of Hg.

b. Preparation of 4-(4-Hydroxybutyl)-2,6-dimethylmorpholine

This intermediate (13.9 g.) was prepared using the procedure described in Example 4b except using 22.9 g. (0.1 mole) of ethyl 4-(2,6-dimethyl-4-morpholinyl)butyrate, 15.2 g. (0.4 mole) of lithium aluminum hydride, and 200 ml. of dimethyl ether and was isolated as a very pale yellow liquid.

c. Preparation of 4-(4-Chlorobutyl)-2,6-dimethylmorpholine Hydrochloride

To a dry flask under a nitrogen atmosphere was added 0.9 g. (4.8 mmoles) of 4-(4-hydroxybutyl)-2,6-dimethylmorpholine in 2.5 ml. of chloroform. The solution was stirred and heated to 40° C. and 0.49 ml. (6.72 mmoles) of thionyl chloride in 2.5 ml. of chloroform was added slowly. The mixture was slowly heated to reflux and held for two hours, then was cooled and diluted with diethyl ether to precipitate the crude product. The crystals were filtered and washed of residual thionyl chloride using diethyl ether to obtain 1.0 g. (85% yield) of 4-(4-chlorobutyl)-2,6-dimethylmorpholine hydrochloride.

d. Preparation of 2-(4-Chlorophenyl)-6-(2,6-dimethyl-4-morpholinyl)capronitrile

This intermediate (400 mg.) was prepared using the procedure described in Example 2a except using 1.0 g. (4.13 mmoles) of 4-(4-chlorobutyl)-2,6-dimethylmorpholine hydrochloride, 1.81 g. (0.021 mole) of sodium hydride, and 3.18 g. (0.021 mole) of 4-chlorobenzyl cyanide in 40 ml. of DMF.

e. Preparation of 1-[2-(4-Chlorophenyl)-2-cyano-6-(2,6-dimethyl-4-morpholinyl)hexyl]-1,2,4-triazole This compound (400 mg.) was prepared using the procedure described in Example 2b except using 400 mg. (1.25 mmoles) of 2-(4-chlorophenyl)-6-(2,6-dimethyl-4-morpholinyl)capronitrile, 0.06 g. (1.38 mmoles) of sodium hydride, 0.15 g. (1.25 mmoles) of 1-(chloromethyl)-1,2,4-triazole, and 4 ml. of DMF and was isolated as a yellow oil.

EXAMPLE 6

Preparation of 1-[2-(4-Chlorophenyl)-2-cyano-13-(2,6-dimethyl-4-morpholinyl)tridecyl]-1,2,4-triazole a. Preparation of Methyl 11-(2,6-Dimethyl-4-morpholinyl)undecylate This intermediate (12.0 g.) was prepared using the procedure described in Example 4a except using 12 g. (0.045 mole) of methyl 11-bromoundecylate, 5.5 ml. (0.045 mole) of 2,6-dimethylmorpholine, 6.12 ml. of triethylamine, and 15 ml. of toluene and was isolated as a yellow, viscous liquid.

b. Preparation of 2,6-Dimethyl-4-(11-hydroxyundecyl)morpholine

This intermediate (9.35 g.) was prepared using the procedure described in Example 4b except using 12 g. (0.038 mole) of methyl 11-(2,6-dimethyl-4-morpholinyl)undecylate, 5.7 g. (0.15 mole) of lithium aluminum hydride, and 100 ml. of dimethyl ether and was isolated as a very light yellow liquid.

c. Preparation of 4-(11-Chloroundecyl)-2,6-dimethylmorpholine

This intermediate (5.1 g.) was prepared using the procedure described in Example 4c except using 9.35 g. (0.033 mole) of 2,6-dimethyl-4-(11-hydroxyundecyl)morpholine, 9.43 g. (0.036 mole) of triphenylphosphine, and 70 ml. of carbon tetrachloride.

d. Preparation of 2-(4-Chlorophenyl)-13-(2,6-dimethyl-4-morpholinyl)tridecanonitrile This intermediate (900 mg.) was prepared using the procedure described in Example 2a except using 3.9 g. (0.013 mole) of 4-(11-chloroundecyl)-2,6-dimethylmorpholine, 0.62 g. (0.014 mole) of sodium hydride, 1.97 g. (0.013 mole) of 4-chlorobenzyl cyanide, and 75 ml. of a 2 to 1 mixture of toluene and DMF.

e. Preparation of 1-[2-(4-Chlorophenyl)-2-cyano-13-(2,6-dimethyl-4-morpholinyl)tridecyl]-1,2,4-triazole This compound (350 mg.) was prepared using the procedure described in Example 2b except using 500 mg. (1.25 mmoles) of 2-(4-chlorophenyl)-13-(2,6-dimethyl-4-morpholinyl)tridecanonitrile, 60 mg (1.35 mmoles) of sodium hydride, 150 mg. (1.25 mmoles) of 1-(chloromethyl)-1,2,4-triazole, and 15 ml. of DMF and was isolated as an amber oil.

EXAMPLE 7

Preparation of 1-[2-(4-Chlorophenyl)-2-cyano-3-(3-pyridyl)propyl]-1,2,4-triazole a. Preparation of 2-(4-Chlorophenyl)-3-(3-pyridyl)acrylonitrile This intermediate (157 g.) was prepared using the procedure described in Example 12a except using 110.0 g. (0.738 mole) of 4-chlorobenzyl cyanide, 81.0 g. (0.74 mole) of 3-pyridinecarboxaldehyde, and 40 ml. of 10% aqueous sodium hydroxide.

b. Preparation of 2-(4-Chlorophenyl)-3-(3-pyridyl)propionitrile

This intermediate (64 g.) was prepared using the procedure described in Example 12b except using 80 g. (0.3 mole) of 2-(4-chlorophenyl)-3-(3-pyridyl)acrylonitrile, and 14 g. (0.36 mole) of sodium borohydride.

c. Preparation of 1-[2-(4-Chlorophenyl)-2-cyano-3-(3-pyridyl)propyl]-1,2,4-triazole This compound (2.3 g.) was prepared using the procedure described in Example 12c except using 3.0 g. (0.0124 mole) of 2-(4-chlorophenyl)-3-(3-pyridyl)propionitrile, 1.48 g. (0.037 mole) of sodium hydride, and 3.0 g. (0.019 mole) of 1-(chloromethyl)-1,2,4-triazole hydrochloride and was isolated as a gummy solid.

EXAMPLE 8

Preparation of 1-[2-(4-Chlorophenyl)-2-cyano-4-(2-thienyl)butyl]-1,2,4-triazole a. Preparation of 2-(2-Thienyl)ethyl Methanesulfonate To a flask was added 25.6 g. (0.20 mole) of 2-(2-thienyl)ethanol in 75 ml. of THF followed by 40.47 g. (0.40 mole) of triethylamine in 30 ml. of THF. The mixture was cooled to 5° C. and 34.4 g. (0.3 mole) of methanesulfonyl chloride in 20 ml. of THF was added dropwise over 20 minutes. The mixture exothermed to 20° C. and was kept at 20° C. during the methanesulfonyl chloride addition. An additional 150 ml. of THF was added to reduce the viscosity of the mixture after a precipitate had formed. After two hours, the reaction was quenched by the addition of 25 ml. of water which was followed by 25 ml of 10% aqueous hydrochloric acid and 200 ml. of ether. The ether layer was separated, washed with 50 ml. of 10% aqueous hydrochloric acid and twice with 75 ml. of saturated aqueous sodium bicarbonate solution, dried, and concentrated to give the 2-(2-thienyl)ethyl methanesulfonate, 38.0 g. (92.2% yield), as an oil.

b. Preparation of 2-(4-Chlorophenyl)-4-(2-thienyl)-butyronitrile

To a flask under a nitrogen atmosphere was added, with stirring, 3.3 g. (0.0825 mole) of 60% sodium hydride, washed twice with hexane to remove the original mineral oil, in 75 ml. of a dry 2 to 1 mixture of DMF and toluene. To this slurry at room temperature was added 11.30 g. (0.075 mole) of 4-chlorobenzyl cyanide in 40 ml. of DMF. After 1.5 hours, the mixture was cooled to 10° C. and 13.7 g. (0.0782 mole) of 2-(2-thienyl)ethyl methanesulfonate in 25 ml. of DMF was added dropwise. The reaction was stirred at room temperature for 13 hours. Then aqueous 10% hydrochloric acid, 20 ml., was added followed by 150 ml. of diethyl ether which was washed three times with 50 ml. portions of water. After drying the ether and concentrating, the product was distilled at 130°–150° C. at 1–2 mm of Hg yielding 2-(4-chlorophenyl)-4-(2-thienyl)butyronitrile as an oil.

c. Preparation of 1-[2-(4-Chlorophenyl)-2-cyano-4-(2-thienyl)butyl]-1,2,4-triazole To a flask under a nitrogen atmosphere was added, with stirring, 1.5 g. (0.036 mole) of 60% sodium hydride, washed twice with hexane to remove the original mineral oil, in 30 ml. of dry DMF. To this slurry at room temperature was added 3.36 g. (12.8 mmoles) of 2-(4-chlorophenyl)-4-(2-thienyl)butyronitrile in 30 ml. of DMF over 10 minutes. After stirring for 30 minutes, 2.15 g. (14.08 mmoles) of 1-(chloromethyl)-1,2,4-triazole hydrochloride was added in two portions and stirred for another 60 minutes. Water, 20 ml., was then added followed by 100 ml. of ether. The ether layer was washed twice with 50 ml. portions of water and the water washes further extracted with 50 ml. of ether. The combined ether extracts were chromatographed on 50 g. of silica gel. The product was eluted with ethyl acetate yielding 1.17 g. of product as a thick brown oil.

EXAMPLE 9

Preparation of 1-[2-Cyano-2-(2-methoxyphenyl)-3-(2-pyridyl)propyl]-1,2,4-triazole a. Preparation of 2-(2-Methoxyphenyl)-3-(2-pyridyl)propionitrile This intermediate (80 g.) was prepared using the procedure described in Example 14a except using 50 g. (0.339 mole) of (2-methoxyphenyl)acetonitrile, 56 g. (0.339 mole) of 2-(chloromethyl)pyridine hydrochloride, 60 g. (0.746 mole) of 50% aqueous sodium hydroxide, and 200 ml. of DMSO.

b. Preparation of 1-[2-Cyano-2-(2-methoxyphenyl)-3-(2-pyridyl)propyl]-1,2,4-triazole To a flask was added 5.0 g. (0.021 mole) of 2-(2-methoxyphenyl)-3-(2-pyridyl)propionitrile, 5.0 g. (0.031 mole) of 1-(chloromethyl)-1,2,4-triazole, and 150 ml. of DMSO, followed by 10 g. (0.125 mole) of 50% aqueous sodium hydroxide over 30 minutes. The reaction exothermed to 40° C. and was stirred for an additional two hours. After cooling, water was added and the organic material extracted with ether. The combined ether extracts were then washed with water, dried using magnesium sulfate, filtered, and the ether removed by rotary evaporation to obtain 3.0 g. of organic residue which was recrystallized from ether yielding 1.3 g. of the product as a grey solid, melting point 155°–158° C.

EXAMPLE 10

Preparation of 1-[2-Cyano-2-(2,4-dichlorophenyl)-5-(1-piperidinyl)-pentyl]-1,2,4-triazole a. Preparation of 2-(2,4-Dichlorophenyl)-5-(1-piperidinyl)valeronitrile This intermediate (10 g.) was prepared using the procedure described in Example 14a except using 10.0 g. (0.054 mole) of 2,4-dichlorobenzyl cyanide, 11.0 g. (0.054 mole) of 1-(3-chloropropyl)piperidine hydrochloride, 11.0 g. (0.135 mole) of 50% aqueous sodium hydroxide, and 50 ml. of DMSO.

b. Preparation of 1-[2-Cyano-2-(2,4-dichlorophenyl)-5-(1-piperidinyl)pentyl]-1,2,4-triazole This compound (5.0 g.) was prepared using the procedure described in Example 9b except using 5.0 g. (0.016 mole) of 2-(2,4-dichlorophenyl)-5-(1-piperidinyl)valeronitrile, 2.7 g. (0.0176 mole) of 1-(chloromethyl)-1,2,4-triazole hydrochloride, 3.2 g. (0.040 mole) of aqueous 50% sodium hydroxide, and 50 ml. of DMSO and was isolated as an oil.

EXAMPLE 11

Preparation of 1-[2-Cyano-2-(2,4-dichlorophenyl)-3-(1-methylpiperidin-3-yl)propyl]-1,2,4-triazole a. Preparation of 2-(2,4-Dichlorophenyl)-3-(1-methylpiperidin-3-yl)propionitrile This intermediate (7.6 g.) was prepared using the procedure described in Example 14a except using 10 g. (0.054 mole) of 2,4-dichlorobenzyl cyanide, 10 g. (0.054 mole) of 3-chloromethyl-1-methylpiperidine hydrochloride, 11 g. (0.135 mole) of aqueous 50% sodium hydroxide, and 100 ml. of DMSO to yield an oil boiling 160°–165° C. at 5 mm of Hg.

b. Preparation of 1-[2-Cyano-2-(2,4-dichlorophenyl)-3-(1-methylpiperidin-3-yl)propyl]-1,2,4-triazole This compound (1.8 g.) was prepared using the procedure described in Example 9b except using 3.0 g. (0.010 mole) of 2-(2,4-dichlorophenyl)-3-(1-methylpiperidin-3-yl)propionitrile, 1.7 g. (0.011 mole) of 1-(chloromethyl)-1,2,4-triazole, 2.0 g. (0.025 mole) of 50% aqueous sodium hydroxide, and 30 ml. of DMSO yielding a white solid, melting point 125°–126° C.

EXAMPLE 12

Preparation of 1-[2-(4-Chlorophenyl)-2-cyano-3-(2-furyl)propyl]-1,2,4-triazole a. Preparation of 2-(4-Chlorophenyl)-3-(2-furyl)acrylonitrile To a flask was added 22.65 g. (0.15 mole) of 4-chlorobenzyl cyanide in 75 ml. of methanol and 14.4 g. (0.15 mole) of 2-furaldehyde in 50 ml. of methanol. While stirring at room temperature, 12.0 g. (0.15 mole) of aqueous 50% sodium hydroxide was added dropwise. Within 30 minutes, a precipitate formed and 50 ml. of additional methanol was added. After one hour, the solid was filtered and dried to give 27.5 g. (91.2% yield) of 2-(4-chlorophenyl)-3-(2-furyl)acrylonitrile as a light yellow solid.

b. Preparation of 2-(4-Chlorophenyl)-3-(2-furyl)propionitrile

To a flask under a nitrogen atmosphere was added 9.24 g. (0.04 mole) of 2-(4-chlorophenyl)-3-(2-furyl)a- crylonitrile in 55 ml. of a 10 to 1 mixture of THF and DMF. While stirring at room temperature, 1.44 g. (0.04 mole) of sodium borohydride in 25 ml. of ethanol was added and the resulting mixture stirred for an additional 18 hours. A mixture of 175 ml. of 6 to 1 methylene chloride and water was added to the reaction while stirring at room temperature. The methylene chloride solution was washed with 10% aqueous hydrochloric acid, dried, and concentrated to give 8.24 g. (90.4% yield) of 2-(4-chlorophenyl)-3-(2-furyl)propionitrile as a thick oil.

c. Preparation of 1-[2-(4-Chlorophenyl)-2-cyano-3-(2-furyl)propyl]-1,2,4-triazole To a flask under a nitrogen atmosphere was added 1.66 g. (0.069 mole) of 60% sodium hydride, which had been washed twice with hexane to remove the mineral oil, in 40 ml. of dry DMF. To this slurry at room temperature was added with stirring 6.40 g. (27.7 mmoles) of 2-(4-chlorophenyl)-3-(2-furyl)propionitrile in 25 ml. of dry DMF. The mixture was stirred for 45 minutes and then 4.66 g. (30.47 mmoles) of 1-(chloromethyl)-1,2,4-triazole hydrochloride was added directly in two portions. The flask contents were stirred for six hours after which 1.6 g. of 60% sodium hydride which had been washed with hexane to remove the oil was added to complete the reaction. Water, 20 ml., was added dropwise followed by 100 ml. of ether and 50 ml. of ethyl acetate. The combined extracts were dried, decolorized with activated charcoal, filtered through infusorial earth, and concentrated to give a thick oil which crystallized on cooling to 3.2 g. (37.1% yield) of 1-[2-(4-chlorophenyl)-2-cyano-3-(2-furyl)propyl]-1,2,4-triazole as a light yellow solid, melting point 112°-114° C.

EXAMPLE 13

Preparation of 1-[2-(4-Chlorophenyl)-2-cyano-3-(2-thienyl)propyl]-1,2,4-triazole a. Preparation of 2-(4-Chlorophenyl)-3-(2-thienyl)acrylonitrile This intermediate (30.3 g.) was prepared using the procedure described in Example 12a except using 22.6 g. (0.15 mole) of 4-chlorobenzyl cyanide, 19.05 g. of 2-thiophenecarboxaldehyde (0.17 mole), and 12 g. (0.15 mole) of 50% aqueous sodium hydroxide and was isolated as a light yellow powder.

b. Preparation of 2-(4-Chlorophenyl)-3-(2-thienyl)propionitrile

This intermediate (9.10 g.) was prepared using the procedure described in Example 12b except using 9.88 g. (0.04 mole) of 2-(4-chlorophenyl)-3-(2-thienyl)acrylonitrile and 1.44 g. (0.04 mole) of sodium borohydride and was isolated as a thick semi-solid.

c. Preparation of 1-[2-(4-Chlorophenyl)-2-cyano-3-(2-thienyl)propyl]-1,2,4-triazole This compound (2.30 g.) was prepared using the procedure described in Example 12c except using 5.44 g. (0.02 mole) of 2-(4-chlorophenyl)-3-(2-thienyl)propionitrile, 2.2 g. (0.09 mole) of sodium hydride, and 3.70 g. (0.02 mole) of 1-(chloromethyl)-1,2,4-triazole and was isolated as a solid with a melting point of 164°-165° C.

EXAMPLE 14

Preparation of 1-[2-Cyano-2-(2-methoxyphenyl)-3-(tetrahydropyran-2-yl)propyl]-1,2,4-triazole a. Preparation of 2-(2-Methoxyphenyl)-3-(tetrahydropyran-2-yl)propionitrile To a flask was added 20 g. (0.1346 mole) of (2-methoxyphenyl)acetonitrile, 25 g. (0.1346 mole) of 2-(bromomethyl)tetrahydro-2H-pyran, and 200 ml. of DMSO. The mixture was stirred for five minutes at room temperature and to the resultant solution was added 22 g. (0.2692 mole) of 50% aqueous sodium hydroxide over 30 minutes with the reaction temperature being allowed to exotherm to 60° C. The reaction was stirred an additional two hours, then cooled, water added and the organic material extracted with ether. The combined ether extracts were then washed with water, dried, filtered, and the ether distilled. The organic residue wss fractionally distilled to obtain 27 g. (82% yield) of the 2-(2-methoxyphenyl)-3-(tetrahydropyran-2-yl)propionitrile boiling 145°-160° C. at 5 mm of Hg.

b. Preparation of 1-[2-Cyano-2-(2-methoxyphenyl)-3-(tetrahydrofuran-2-yl)propyl]-1,2,4-triazole This compound was prepared using the procedure described in Example 2b except using 27.0 g. (0.110 mole) of 2-(2-methoxyphenyl)-3-(tetrahydropyran-2-yl)propionitrile, 6.6 g. (0.165 mole) of 60% sodium hydride which had been washed with hexane to remove the mineral oil originally present, 19 g. (0.165 mole) of 1-(chloromethyl)-1,2,4-triazole, and 400 ml. of a 1 to 1 mixture of DMSO and DMF. The 1-[2-cyano-2-(2-methoxyphenyl)-3-(tetrahydropyran-2-yl)propyl]-1,2,4-triazole, 20.0 g. (56% yield), was obtained as a solid, melting point 120°-121° C.

EXAMPLE 15

Preparation of 1-[2-Cyano-2-phenyl-4-(2-pyridyl)butyl]-1,2,4-triazole a. Preparation of 2-Phenyl-2-(2-pyridyl)butyronitrile To a flask under a nitrogen atmosphere was added, with stirring, 11.71 g. (0.100 mole) of phenylacetonitrile in 20 ml. of DMSO, then 10.51 g. (0.11 mole) of 2-vinylpyridine in 50 ml. of DMSO was added followed by 5.5 g. of a 35.5% potassium hydroxide solution (0.035 mole). After two hours, the reaction mixture was heated to 70° C. for 30 minutes, then quenched by adding 50 ml. of water and 100 ml. of ethyl acetate. The phases were separated and the ethyl acetate phase washed twice with 100 ml. of water. The product mixture was fractionally distilled to obtain 7.3 g. (37% yield) of the 2-phenyl-2-(2-pyridyl)butyronitrile boiling 200°-210° C. at 1 to 2 mm of Hg.

b. Preparation of 1-[2-Cyano-2-phenyl-4-(2-pyridyl)butyl]-1,2,4-triazole

This compound (1.27 g.) was prepared using the procedure described in Example 12c except using 2.53 g. (0.0117 mole) of 2-phenyl-2-(2-pyridyl)butyronitrile, 1.41 g. (0.035 mole) of hexane washed sodium hydride, and 1.98 g. (0.0128 mole) of 1-(chloromethyl)-1,2,4-triazole hydrochloride and was isolated as an oil.

The examples of this invention were tested for fungicidal activity in vivo against cucumber downy mildew (CDM), rice blast (RB), tomato late blight (TLB), wheat leaf rust (WLR), wheat powdery mildew (WPM), and wheat stem rust (WSR). In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2 to 1 to 1 mixture of water, acetone, and methanol, sprayed onto the plants, allowed to dry, and then the plants were inoculated with the fungus 24 hours after spraying. Each test utilized control plants which were sprayed with the water, acetone, and methanol mixture and inoculated with the fungus. The remainder of the technique for each of the tests is given below. Results are reported as percent disease control (percentage of a plant treated with a compound of the present invention lacking disease signs or symptoms compared to an inoculated, untreated control plant).

Cucumber Downy Mildew (CDM):

*Pseudoperonospora cubensis* was maintained on leaves of live Marketeer cucumber plants in a constant temperature room at 65°-75° F. in humid air with moderate light intensity for 7 to 8 days. A water suspension of the spores from infested leaves was obtained and the spore concentration was adjusted to about 100,000 per ml of water.

Marketeer cucumber seedlings previously treated with compounds of this invention were inoculated by spraying the underside of the leaves with the spore concentration using a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65°-75° F. Seven days after inoculation, the percent disease control was determined.

Rice Blast (RB):

M201 rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75°-85° F.) for about 24 hours, then placed in a greenhouse environment (70°-75° F.). Seven to eight days after inoculation, the percent disease control was determined.

Tomato Late Blight (TLB):

*Phytophthora infestans* was cultured on four week old Pixie tomato plants in a controlled environment room (65°-70° F. and 100% relative humidity). After storage, the spores were washed from the leaves with water and dispersed by DeVilbiss atomizer over three week old Pixie tomato plants which had been sprayed 24 hours before with experimental fungicides. The inoculated plants were placed in a humidity cabinet at 70° F. and constant mist for 24 hours for infection. The plants were then moved to the controlled environment room at 65°-70° F. and 100% relative humidity. Disease control levels were recorded as percent control four days after inoculation and five days after spraying the compounds.

Wheat Leaf Rust (WLR):

*Puccinia recondita* (f. sp. *tritici* Races PKB and PLD) was cultured on seven day old wheat (cultivar Fielder) over a 14 day period in the greenhouse. Spores were collected from the leaves, cleaned by sieving through a 250 micron opening screen and stored or used fresh. A spore suspension was prepared from dry uredia by adding 20 mg (9.5 million) per ml of Soltrol oil. The suspension was dispensed into gelatin capsules (0.7 ml capacity) which attach to the oil atomizers. One capsule was used to inoculate a flat of twenty of the two inch square pots of seven day old Fielder wheat. The plants were placed in a dark mist chamber (18°-20° C. and 100% relative humidity) for 24 hours. The plants were then put in the greenhouse for the latent period and scored after 10 days for disease levels. Protective and curative tests were inoculated one day after and two days, respectively, before spraying the plants with the test chemicals.

Wheat Powdery Mildew (WPM):

*Erysiphe graminis* (f. sp. *tritici*) was cultured on Hart wheat seedlings in a controlled temperature room at 65°-75° F. Mildew spores were shaken from the culture plants onto Hart wheat seedlings which had been sprayed previously with the fungicide compound. The inoculated seedlings were kept in a controlled temperature room at 65°-75° F. and subirrigated. The percent disease control was rated eight days after the inoculation.

Wheat Stem Rust (WSR):

*Puccinia graminis* (f. sp. *tritici* Race 15B-2) was cultured on Tyler wheat seedlings for a period of 14 days in a greenhouse. The remainder of the test protocol was conducted as previously described for wheat leaf rust.

Table 3 lists fungicidal data for Examples 1-15 of the present invention.

TABLE 3

| | Fungicide Test Results[1] | | | | | |
|---|---|---|---|---|---|---|
| Ex. No. | CDM | RB | TLB | WLR | WPM | WSR |
| 1 | 10/225 | 100/225 | 5/225 | 100/225 | 100/225 | —/—[2] |
| 2 | 0/300 | 0/300 | 0/300 | —/— | 50/300 | 0/300 |
| 3 | 0/300 | 0/300 | 0/300 | —/— | 0/300 | 50/300 |
| 4 | 0/300 | 0/300 | 0/300 | —/— | 0/300 | 100/300 |
| 5 | 0/300 | 0/300 | 0/300 | —/— | 0/300 | 80/300 |
| 6 | 0/300 | 0/300 | 0/300 | —/— | 0/300 | 80/300 |
| 7 | —/— | 0/150 | 0/150 | 0/150 | 85/150 | —/— |
| 8 | 100/150 | 0/150 | 80/150 | 95/150 | 95/150 | 95/150 |
| 9 | —/— | 0/150 | 100/150 | 0/150 | 0/150 | —/— |
| 10 | —/— | 50/300 | —/— | 25/300 | 75/300 | —/— |
| 11 | 50/300 | 0/300 | 0/300 | 25/300 | 95/300 | —/— |
| 12 | —/— | —/— | 80/150 | 0/150 | 100/150 | 50/150 |
| 13 | 0/300 | 0/300 | 0/150 | 0/150 | 100/150 | 100/150 |
| 14 | 0/300 | 0/300 | 0/300 | 0/300 | 99/300 | —/— |
| 15 | 0/300 | —/— | 85/300 | 0/300 | 85/300 | —/— |

[1]Values Given as (% Control)/(Grams/Hectare) Application Rate.
[2]Not Tested.

The 1,2,4-triazoles, and the enantiomorphs, geometric isomers, acid addition salts and metal salt complexes thereof of this invention are useful as agricultural fungicides and as such can be applied to various loci such as the seed, the soil or the foliage. These compounds as a class show broad spectrum antifungal activity when applied to cereal grains such as wheat, barley, rye and rice, peanuts, beans, grapes, turf, fruit orchards, vegetables and golf courses. The compounds of this invention are especially strong against powdery mildews, rusts, and Helminthosporium diseases in cereal crops such as wheat, barley, rye, or rice. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, suspension concentrates, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, DMF, pyridine or DMSO and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90%, and in flowable emulsion concentrates, can be as high as about 75%.

Wettable powders, suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 5% to about 98%, preferably from about 25% to about 75%. A typical wettable powder is made by blending 50 parts of a 1,2,4-triazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ® 7.

Dusts are prepared by mixing the 1,2,4-triazoles, or the enantiomorphs, geometric isomers, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to a range of about 1% to about 10% use concentration.

The 1,2,4-triazoles, and the enantiomorphs, geometric isomers, salts and complexes thereof can be applied as fungicidal sprays by methods commonly employed, such as conventional high gallonage hydraulic sprays, low gallonage sprays, air blast sprays, aerial sprays and dusts. The dilution and rate of application will depend upon the type of equipment employed, the method of application and diseases to be controlled, but the effective amount is usually from about 0.05 pound to about 5.0 pounds of the active ingredient per acre.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.05 to about 5.0 pounds per acre. As a foliar fungicide, the toxicant is usually applied to growing plants at a rate of from about 0.25 to about 1.0 pound per acre.

Fungicides which can be combined with the fungicides of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isozxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, α-[2-(4-chlorophenyl)ethyl]-α-phenyl-1H-1,2,4-triazole-1-propanenitrile, hexaconazole, cyprconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

We claim:

1. A triazole compound having the formula:

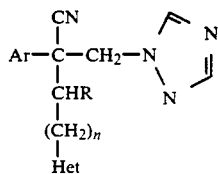

wherein Ar is selected from phenyl, 4-chlorophenyl, 4-fluorophenyl, 2-methoxyphenyl, 2,4-dichlorophenyl and 2,4-difluorophenyl; R is hydrogen or methyl; n is zero or an integer from one to about twenty; and Het is selected from tetrahydrofuran-2-yl, 4-morpholinyl, 2,6-dimethyl-4-morpholinyl, 2-thienyl, piperidin-1-yl, and 1-methylpiperidin-3-yl.

2. The compound of claim 1 wherein R is hydrogen and n is zero or an integer from one to eleven, and Ar is selected from phenyl, 4-chlorophenyl, 2-methoxyphenyl and 2,4-dichlorophenyl.

3. The compound of claim 2 wherein Het is tetrahydrofuran-2-yl and n is one.

4. The compound of claim 2 wherein Het is 4-morpholinyl or 2,6-dimethyl-4-morpholinyl and n is from two to eleven.

5. The compound of claim 2 wherein Het is 2-thienyl, n is one or two and Ar is 4-chlorophenyl.

6. The compound of claim 2 wherein Het is piperidin-1-yl or 1-methylpiperidin-3-yl, n is from one to three and Ar is 2,4-dichlorophenyl.

7. A fungicidal composition for controlling phytopathogenic fungi which comprises an agronomically acceptable carrier and a fungicidally effective amount of the compound of claim 1.

8. A method for controlling phytopathogenic fungi which comprises applying to the locus where control is desired a fungicidally effective amount of the compound of claim 1.

* * * * *